United States Patent [19]

Neumann

[11] Patent Number: 4,824,248
[45] Date of Patent: Apr. 25, 1989

[54] STABILIZED SENSOR DEVICE

[75] Inventor: Catharine G. Neumann, Southfield, Mich.

[73] Assignee: Environmental Research Institute of Michigan, Ann Arbor, Mich.

[21] Appl. No.: 135,256

[22] Filed: Dec. 21, 1987

[51] Int. Cl.[4] ...................... G01N 21/01; G01N 21/86
[52] U.S. Cl. .................................... 356/244; 350/255; 356/429; 356/445
[58] Field of Search ............... 356/244, 429, 430, 432, 356/445, 350; 384/12; 406/88, 92; 350/255

[56] References Cited

U.S. PATENT DOCUMENTS 3,890,049  6/1975  Collins et al. ....................... 356/429
3,902,769  9/1975  Neumann et al. .................... 384/12
4,030,815  6/1977  Andrevski et al. .................. 350/255
4,277,177  7/1981  Larsen et al. ..................... 350/571 X Primary Examiner—Vincent P. McGraw
Attorney, Agent, or Firm—Krass & Young

[57] ABSTRACT

An optical sensor includes a vortex diffuser bearing for support of the optical elements thereof in a fixed, spaced apart and angular relationship relative to a subjacent surface. The sensors are readily adapted to be fabricated into matrices adapted for high volume scanning of surfaces, as for example to detect irregularities in the coatings thereof. The sensors are also adaptable for use in photogrammetry, microdensitometry, or other applications wherein precise, stable and repeatable positioning is required.

18 Claims, 2 Drawing Sheets

STABILIZED SENSOR DEVICE

FIELD OF THE INVENTION

This invention relates generally to sensors and particularly to optical sensors adapted to be maintained in close and constant proximity to a surface for inspection, measurement or other quantification thereof. The present invention most particularly relates to vortex stabilized optical sensors adapted to be positioned in precise spaced apart and angular relationship with a subjacent surface.

BACKGROUND OF THE INVENTION

In many operations it is desirable to position and maintain a sensor element in close, but non-contacting, reliably constant proximity to a surface. For example, in high volume industrial production processes surface inspection techniques are widely utilized to assess various physical properties of painted, polished, electroplated or otherwise finished surfaces. Towards this end properties such as reflectance, light absorption, light transmission, haze and color value are frequently measured by optical sensors.

In most instances, it is desirable that these optical sensors be maintained in relatively close and repeatably constant proximity, and at a fixed angular relationship to the surface being inspected so as to allow for reliable and repeatable collection of data. It is also generally desired that the sensors be disposed in a non-contacting relationship so as to allow for high volume passage of the materials being inspected therepast, while avoiding marring or scratching of finished surfaces.

The need for precise and repeatable sensor positioning is not soley restricted to high volume industrial processes, but also arises in the taking of precision measurements. For example, analysis of photographic data frequently involves microdensitometry, photogrammetry or high resolution scanning for the digitization of images. In all of these processes, an optical sensor is disposed in close proximity to a photographic print or transparency, and moved thereacross. Obviously, in the taking of such precision measurements it is required that a precise sensor-object spacing and angular relationship be maintained and, it is further required that such precise positional relationship be repeatably obtained in subsequent measurements.

It should thus be appreciated that accurate placement of optical sensors is required in many applications ranging from high volume industrial processes to precise and constant measurement techniques, as well as will involve maintaining precise sensor-object distance as well as a constant sensor-object angle. By analogy, it will also be appreciated that precise positioning of other types of sensors such as capacitive sensors, magnetic snesors and the like will also be critical in many applications. It is further desirable, and absolutely necessary in many instances, to employ a non-contact method for maintaining the precise sensor-object positional relationship.

In those instances where mechanical complexity of the sensor device is no object and cost is no limitation, there are various technology intensive solutions to the problem of maintaining sensor position. Micropositioning apparatus of various designs are presently commercially available, however such equipment generally is expensive to purchase, and time consuming to operate. U.S. Pat. No. 3,722,996 discloses a step and repeat photo mask generating apparatus wherein precise positioning of the various optical components thereof is maintained by a hydraulic feedback loop adapted to control an air bearing. A position sensor is disposed to regulate the amount of gas provided to the bearing so as to vary the spacing between the apparatus and the subjacent surface. While this type of feedback controlled air bearing system does maintain a desired positional relationship its cost and mechanical complexity precludes its use in a high volume industrial setting.

U.S. Pat. No. 3,218,108 discloses a positioning apparatus supported by air bearings. As detailed therein, a set of air bearings is utilized solely to support and smoothly translate a work stage. The air bearings are not employed to maintain a fixed distance between the work stage and the underlying surface but rather are employed in conjunction with mechanical positioners to move the work stage in the X and Y directions.

It should be seen then that there is a need for a simple, inexpensive method and apparatus wherein sensors and the like can be rapidly precisely and repeatedly positioned relative to a subjacent surface. It is further desired that such method and apparatus will permit non-contact positioning of sensors and will be adaptable for use in a high volume, continuous process.

The present invention provides a vortex stabilized sensor system wherein an optical or other type sensor is maintained in precise spatial and angular relationship relative to a subjacent surface irrespective of dynamically changing conditions. The sensors of the present invention may be disposed to scan or inspect moving surfaces as for example in a high volume production process or may be disposed to accomplish detailed measurement of surface characteristics with a high degree of precision. The sensors of the present invention are readily adaptable for use in a large area matrix adapted to accomplish numerous, simultaneous measurements. These and other advantages of the present invention will be apparent from the drawings and description which follow.

SUMMARY OF THE INVENTION

There is disclosed herein an optical sensor adapted to be stabilized in a fixed, spaced apart and angular relationship relative to a subjacent surface and including at least one optical element. Further included in the sensor is a bearing member adapted to retainably support the optical member and having a cavity defined therein. The cavity includes a side wall and is open at the bottom. The sensor further includes means adapted to introduce a fluid stream into the cavity such that the fluid follows a helical path of travel therethrough and exits through the open bottom so that a high pressure region is created proximate the wall of the cavity and a low pressure region is created proximate the center of the cavity. The high and low pressure regions cooperateto maintain the bearing member and the optical element associated therewith in a fixed, spaced apart and angular relationship with a surface disposed proximate the bottom of the cavity. The optical element may include a fiber optic element such as a single fiber or a fiber bundle and may be disposed in optical communication with another optical element remote from the bearing member.

The optical element may include a source of illumination and/or a photodetector and may further include one or more lenses. The optical sensor may be adapted to measure light reflected from or transmitted through a surface proximate thereto. In one embodiment, the optical element may be disposed within the cavity, whereas in other embodiments, the optical elements may be disposed outside the cavity.

The cavity may be a cylindrical cavity or it may be configured as a portion of a sphere. In some instances, the cavity may be an irregularly shaped cavity. The bearing member may be at least partially flexible so as to allow the sensor to conform to a variety of irregular surfaces. In a particular embodiment, the bearing member may include a plurality of cavities, each having at least one optical element associated proximate thereto.

The fluid introduction means may comprise means adapted to introduce a gas and may include a plurality of inlets. In a particular embodiment, the cavity is of a generally circular cross section and the inlets are disposed so as to introduce a fluid stream in a direction substantially tangent to the circumference of the circular cavity.

DETAILED DESCRIPTION OF THE INVENTION

It has been found in accord with the principles of the present invention that a vortex diffuser bearing may be employed to stabilize a sensor element in a fixed spaced apart and angular relationship relative to a subjacent surface. The vortex bearing is a type of fluid bearing wherein the fluid is introduced into a cavity in a stream directed in such a manner so as to create a helical swirl therein. As will be described in greater detail hereinbelow, this unique pattern of fluid flow stabilizes the bearing relative to a subjacent surface and serves to maintain a fixed spatial and angular relationship over a wide range of fluid flow rates.

Figure 1:
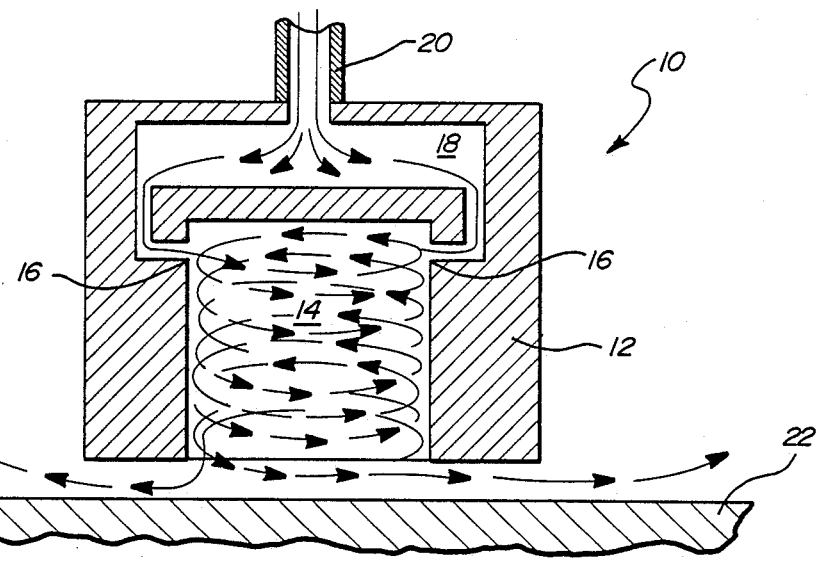
FIG. 1 is a cross-sectional view of a vortex diffuser bearing which may be employed in the practice of the present invention.

Referring now to FIG. 1, there is shown in cross section a stylized depiction of a particular vortex diffuser bearing 10 which may be employed in the practice of the present invention. The bearing 10 includes a bearing member 12 having a cavity 14 defined therein. As depicted, the cavity 14 is a generally cylindrical cavity although other shapes such as hemispheres, other partial spherical sections, irregular sections and the like may be similarly employed. The bearing member 12 further includes fluid introduction ports 16 communicating with the cavity 14 and a fluid supply manifold 18 having a supply conduit 20 associated therewith.

The inlets 16 are disposed relative to the cavity 14 such that the fluid introduced thereinto is directed in a generally helical path of travel as indicated by the arrows. This swirling of fluid creates a vortex within the cavity causing the fluid molecules to concentrate along the side walls of the cavity 14 prior to their exit from the bottom surface thereof. This vortex tends to create a high pressure region proximate the walls of the cavity and a low pressure region proximate the center of the cavity. The high pressure region and the low pressure region cooperate to provide a dynamic equilibrium which serves to draw a subjacent surface 22 toward the cavity and maintain that surface 22 at a fixed distance from the bearing member 12. What is notable about this phenomenon is that the gap between the bearing member 12 and the subjacent surface 22 (and hence the spacing and angular relationship thereof) is quite constant over a wide range of fluid flows. This is because as the fluid flow increases the pressure in the high pressure region increases and the pressure in the low pressure region decreases, thus maintaining a dynamic equilibrium which ensures a constant spatial relationship.

Figure 2:
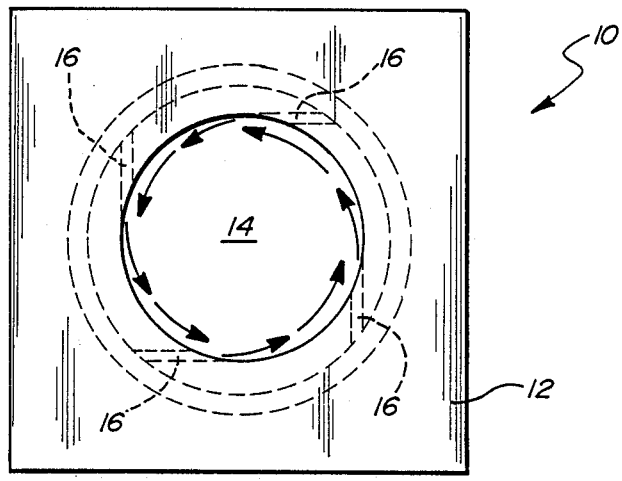
FIG. 2 is a bottom plan view of the bearing of FIG. 1.

Referring now to FIG. 2, there is shown a bottom plan view of the vortex diffuser bearing 10 of FIG. 1 illustrating the bottom surface of the bearing member 12, the cavity 14, and the helical flow of fluid as indicated by the curved arrows. Also shown in phantom outline are four gas inlets 16, disposed so as to introduce a helical flow of fluid into the cavity 14. It should be noted that while four inlets 16 are depicted a larger or smaller number may be similarly employed, the only criterion being that the inlets be disposed so as to create the helical path of fluid travel within the cavity 14. As shown, the cavity 14 is of circular cross section however the principles disclosed herein are operative with cavities of other configurations provided that helical flow through at least a portion thereof can be sustained.

It should be noted that a large number of various fluid bearings of different designs have been known and employed for numerous years for a variety of purposes. Not all such bearings are suitable for use with the present invention insofar as the spatial separation maintained between many of such bearings and the subjacent surface upon which they are supported is a direct function of pressure of the fluid therein. Accordingly, the present invention contemplates utilizing vortex type bearings wherein a helical flow of fluid is established. One configuration of such bearings is disclosed in U.S. Pat. Nos. 3,782,791; 3,902,768; 3,902,769 and 3,904,255 the disclosures of which are incorporated herein by reference.

Figure 3:
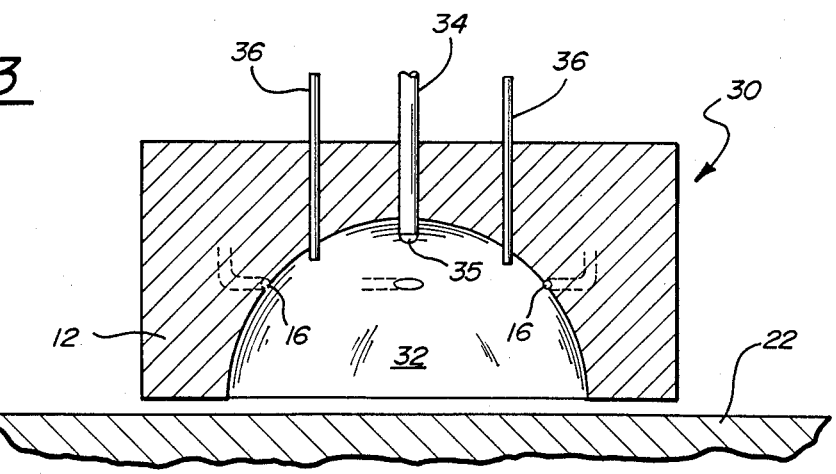
FIG. 3 is a cross-sectional view of a sensor of the present invention.

Referring now to FIG. 3, there is shown an optical sensor structured in accord with the principles of the present invention. The sensor 30 of FIG. 3 includes a bearing member 12, generally similar to that described with reference to FIGS. 1 and 2. Defined by the bearing member 12 is a cavity 32, depicted in this instances as a hemispherical cavity, it being kept in mind that cylindrical cavities or cavities of other shapes may be similarly employed.

Projecting into the cavity 32, are a number of optical elements. In the central portion of the cavity is a source of illumination 34, which in this instance is a fiber optic element operatively communicating with an external source of illumination and including a lens 35 on the terminal portion thereof. The fiber optic element 34 may be a single fiber or a fiber bundle and is adapted to illuminate the surface of an object 22 under inspection.

As depicted the sensor 30 of FIG. 3 further includes a pair of light receiving elements 36 disposed so as to collect light reflected from the surface of the object 22. The light receiving elements 36 may also be fiber optic elements operatively communicating with photosensor elements such as photo diodes, photo transistors and the like disposed externally of the sensor. In some instances it may be desirable to include a lens or other element in association with the light receiving elements 36 to assist in the collection and transmission of the reflected light. It should be noted that numerous modifications of the optical system may be had in accord with the principles of the instant invention. For example, the light receiving elements 36 may be greater or fewer in number and may include photosensitive elements mounted directly within the bearing member 12 itself. Furthermore, the light source 34 may comprise a light emitting source also mounted within the cavity 32 and toward this end may include a microminiature lightbulb, a light emitting diode or other such light source.

The cavity 32 of the sensor 30 is provided with fluid inlets 16, adapted to provide a helical flow of fluid therethrough as previously described. Although not illustrated, the fluid inlet 16 will obviously communicate with an external fluid source as previously described. In operation, the sensor 30 of FIG. 3 is provided with a flow of an appropriate fluid via fluid inlets 16. This flow serves to stabilize the sensor 30 in a fixed, spaced apart and angular relationship with the surface 22 undergoing inspection. Because the sensor 30 is supported on a fluid film it may be readily moved back and forth across the surface and the unique characteristics resulting from the vortex flow therethrough serve to maintain the sensor 30 at a fixed distance from the surface 22 and furthermore serve to maintain a fixed angular relationship between the optical element 34 and 36 and the surface of the object 22.

Figure 4:
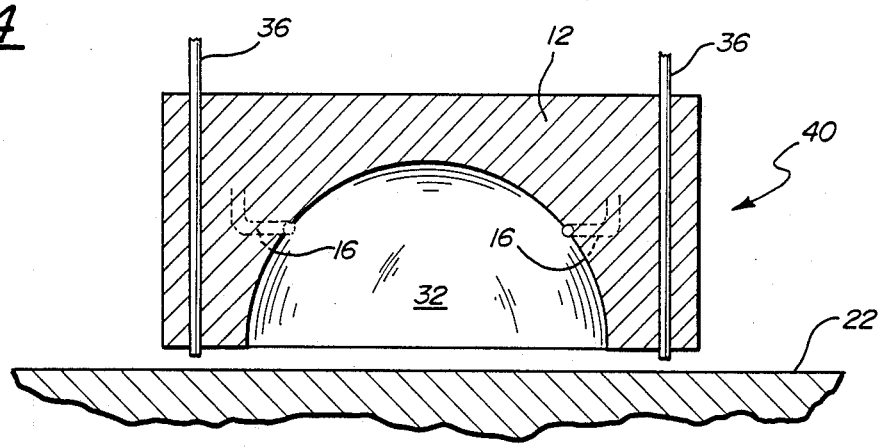
FIG. 4 is a cross-sectional view of an alternative embodiment of a sensor structured in accord with the principles of the present invention.

Referring now to FIG. 4, there is shown an alternative structure for an optical sensor 40 in accord with the principles of the present invention. The elements of the sensor 40 of FIG. 4 are generally similar to those described with reference to FIG. 3 and accordingly will be referred to by similar reference numerals. The sensor 40 includes a bearing member 12 having a central cavity 32 formed therein and including fluid inlet means 16 disposed to create a helical flow of fluid therethrough. Where the sensor 40 of FIG. 4 differs from the sensor of FIG. 3 is in that the optical elements are not mounted within the cavity 32, but are disposed adjacent thereto. As shown, a pair of optical elements 36 are disposed so as to be maintained in spaced apart relationship with the surface of an object 22 under inspection. As depicted the optical elements 36 are light receiving elements generally similar to those previously described. Such an embodiment is well suited in those instances where the object 22 under inspection is light emitting, that is to say the object 22 is a transparent or translucent member which is lit from the bottom side thereof. In those instances where an opaque object 22 is being inspected a source of illumination must be provided and toward that end an additional light source may be disposed adjacent the optical receiving element 36. In some instances a single fiber optic element may be utilized in a multiplex manner to both illuminate an object and receive light reflected therefrom.

Figure 5:
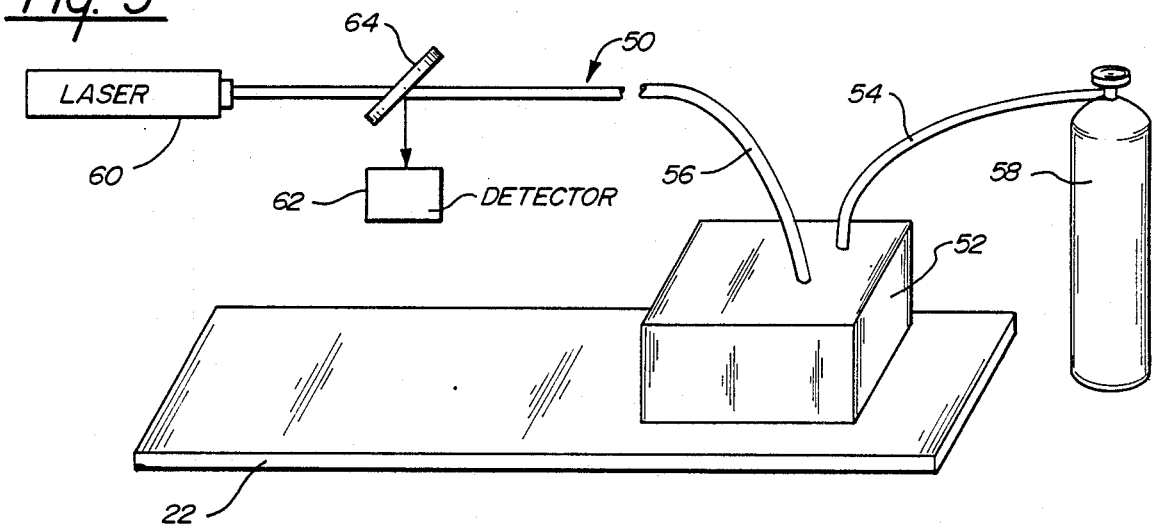
FIG. 5 is a stylized depiction of a surface inspection apparatus structured in a accord with the principles of the present invention.

Referring now to FIG. 5 there is shown a stylized apparatus 50 as disposed to inspect a surface of an object 22. As depicted the apparatus 50 includes a sensor head 52 having gas supply 54 and fiber optic communication link 56 associated therewith.

The sensor head 52 includes at least one optical sensor generally similar to those previously described. The gas supply line 54 is in communication with a source of gas such as a cylinder 58 so as to provide for the helical flow through the cavity portion of the sensor head 52 so as to maintain the head 52 in fixed positional and angular relationship with the surface of the object 22. The fiber optic link 56 is utilized to provide illumination via a light source such as the laser 60. The fiber optic link 56 is also employed to return reflected light from the surface 52 to a detector 62. Toward this end the fiber optic link 56 will include a beam splitter or diverter device 64 therein. Alternatively, a plurality of fiber optic links may be utilized to separate the illumination and detection functions.

Figure 6:
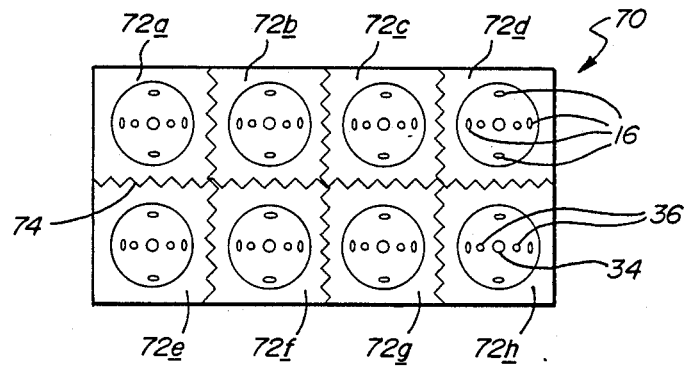
FIG. 6 is a bottom plan view of an array of sensors structured in accord with the principles of the present invention.

The sensors of the present invention may be structured in a matrix form so as to provide for the taking of a plurality of simultaneous measurements from a surface. Referring now to FIG. 6, there is shown one such matrix of sensors in a bottom plan view. The matrix 70 is shown as comprised of eight separate sensor units 72a–72h, each generally similar to that depicted with reference to FIG. 3. Accordingly each sensor unit 72 includes a light source 34, light receiving elements 36 and four fluid inlet openings 16. The individual sensor elements 72 are all joined together in a manner which allows for relative flexual motion therebetween so as to enable the array 70 to conform to variously shaped surfaces. In some instances the bearing member forming each of the sensor units 72 may be fabricated from a flexible material, such as a polymeric material and the entire unit 70 may be made flexible. In other instances, the individual sensor units 72a will each be formed with a rigid bearing member and the individual sensor units 72 will be joined to form a matrix by means of a flexible coupling 74, such as a hinge or a flexible polymeric binding member.

Figure 7:
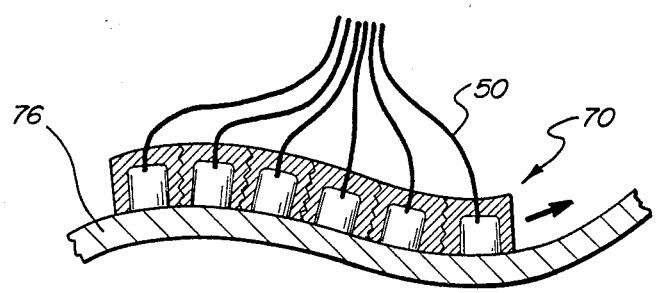
FIG. 7 is a cross-sectional view of the sensor array of FIG. 6 as operatively deployed to inspect an irregularly contoured surface.

Referring now to FIG. 7 there is shown a side view of the sensor matrix unit 70 of FIG. 6 as disposed upon an irregularly shaped surface 76. As depicted the unit 70 includes a plurality of fiber optic elements 50 communicating with each of the sensor units 72a in a manner as described in FIG. 5. Although not illustrated, the sensor matrix 70 will obviously also have a fluid supply communicating therewith as previously described.

An embodiment as illustrated in FIG. 7 is readily adapted for inspection of surfaces in a manufacturing environment; as for example the matrix 70 may be utilized for measuring microscopic texture, quality of coating finish and similar parameters. The individual sensor units are adapted to be stably and reliably positioned with respect to the surface by the vortices therein and accordingly the sensor matrix 70 readily conforms to and follows even irregular surfaces maintaining optical alignment therewith.

Obviously, many other modifications of the present invention will be apparent to one of skill in the art in light of the disclosure herein. For example, the principles disclosed may be employed in conjunction with sensors other than optical sensors. For example, film thickness is often determined by the use of capacitance measurements and accordingly, an arrangement such as that illustrated herein may be utilized to precisely place a capacitance sensor at a given distance from a surface. Similarly, magnetic measurements may be reliably accomplished.

While the operation of the vortex diffuser has been described primarily with reference to use of gaseous fluid medium the present invention is obviously not so limited but may be employed with any fluid. For example, in some instances it may be desirable to utilize an aqueous or non-aqueous fluid, as for example when ultrasonic rather than optical measurements are being made. In such instances, the liquid medium can provide for transmission of ultrasonic energy while supplying the vortex necessary for stabilization. These and other variations will be obvious in light of the foregoing drawings, description and discussion. Accordingly, the foregoing are not meant to be limitations upon the practice of the present invention but illustrations thereof. It is the following claims, including all equivalents, which define the scope of the present invention.

I claim:

1. An optical sensor adapted to be stabilized in a fixed, spaced apart and angular relationship relative to a subjacent surface, said sensor including:
    at least one optical element;
    a bearing member adapted to retainably support the optical element, said bearing member having a cavity defined therein, said cavity including a side wall and being open at the bottom, which is disposed proximate the subjacent surface; and
    means adapted to introduce a fluid stream into the cavity such that the fluid follows a helical path of travel therethrough and exits through the bottom thereof, so that a high pressure region is created proximate the wall of the cavity and a low pressure region is created proximate the center of the cavity, whereby said high and low pressure regions cooperate to maintain said bearing member and optical element in a fixed, spaced apart and angular relationship with said subjacent surface.

2. A sensor as in claim 1, wherein said optical element includes a fiber optic element.

3. An optical sensor as in claim 2, wherein said fiber optic element is in optical communication with another optical element disposed remote from the bearing member.

4. A sensor as in claim 1, wherein said optical element includes a source of illumination.

5. A sensor as in claim 1, wherein said optical element includes a photodetector.

6. A sensor as in claim 1, wherein said optical element includes a lens.

7. An optical sensor as in claim 1, wherein said optical element is adapted to measure light reflected from the subjacent surface.

8. A sensor as in claim 1, wherein said optical element is adapted to measure light absorbed by the subjacent surface.

9. A sensor as in claim 1, wherein said optical element is adapted to measure light transmitted by said subjacent surface.

10. A sensor as in claim 1, wherein said optical element is disposed within the cavity.

11. A sensor as in claim 1, wherein said optical element is disposed outside the cavity.

12. A sensor as in claim 1, wherein said bearing member defines a substantially cylindrical cavity.

13. A sensor as in claim 1, wherein said bearing member defines a cavity which is portion of a sphere.

14. A sensor as in claim 1, wherein said bearing member is at least partially flexible.

15. A sensor as in claim 1, wherein said bearing member includes a plurality of cavities, each having at least one optical element associated proximate thereto.

16. A sensor as in claim 1, wherein said fluid introduction means is adapted to introduce a gas.

17. A sensor as in claim 1, wherein said fluid introduction means includes a plurality of inlets.

18. A sensor as in claim 17, wherein said cavity is of a generally circular cross section and said inlets are adapted to introduce the fluid stream in a direction substantially tangent to the circumference of the circular cavity.

* * * * *